(12) United States Patent
Chen et al.

(10) Patent No.: US 8,538,214 B2
(45) Date of Patent: Sep. 17, 2013

(54) OPTICAL RESONATOR AND OPTICAL SENSING SYSTEM COMPRISING THE SAME

(75) Inventors: Xian Tong Chen, Singapore (SG); Shao Hua Tao, Singapore (SG); Guo-Qiang Patrick Lo, Singapore (SG); Shi Yang Zhu, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 296 days.

(21) Appl. No.: 12/993,325

(22) PCT Filed: Jun. 29, 2008

(86) PCT No.: PCT/SG2008/000198
§ 371 (c)(1),
(2), (4) Date: Feb. 11, 2011

(87) PCT Pub. No.: WO2009/145731
PCT Pub. Date: Dec. 3, 2009

(65) Prior Publication Data
US 2011/0149285 A1    Jun. 23, 2011

(51) Int. Cl.
*G02B 6/26* (2006.01)
(52) U.S. Cl.
USPC ............. 385/50; 385/15; 385/31; 385/32; 385/39; 385/51

(58) Field of Classification Search
USPC .............. 385/15, 31, 32, 39, 50, 51
See application file for complete search history.

(56) References Cited

U.S. PATENT DOCUMENTS

| | | | |
|---|---|---|---|
| 7,145,660 B2 | 12/2006 | Margalit et al. | |
| 7,327,460 B2* | 2/2008 | Sanders et al. | 356/461 |
| 7,612,887 B2* | 11/2009 | Choi et al. | 356/481 |
| 7,903,240 B2* | 3/2011 | Smith et al. | 356/39 |
| 2007/0237460 A1 | 10/2007 | Fan et al. | |

FOREIGN PATENT DOCUMENTS

WO    2008054170 A1    5/2008

OTHER PUBLICATIONS

Armani, A. et al., "Label-Free, Single-Molecule Detection with Optical Microcavities", "Science", Aug. 10, 2007, pp. 783-787, vol. 317.

* cited by examiner

*Primary Examiner* — Jennifer Doan
(74) *Attorney, Agent, or Firm* — Hultquist, PLLC; Steven J. Hultquist

(57) ABSTRACT

An embodiment of the invention relates to an optical resonator. The optical resonator includes an input optical waveguide and a closed loop coupled to the input optical waveguide. The closed loop is adapted to receive light from the input optical waveguide, wherein the closed loop includes at least one hole formed within a portion of the closed loop.

19 Claims, 12 Drawing Sheets

(a)

(b)

(c)

(a)

(b)

OPTICAL RESONATOR AND OPTICAL SENSING SYSTEM COMPRISING THE SAME

CROSS-REFERENCE TO RELATED APPLICATIONS

This application is a U.S. national phase application under the provisions of 35 U.S.C. §371 of International Patent Application No. PCT/SG08/00198 filed May 29, 2008. The disclosure of such international patent application is hereby incorporated herein by reference in its entirety, for all purposes.

FIELD OF THE INVENTION

Embodiments of the invention generally relate to an optical resonator and an optical sensing system comprising the same.

BACKGROUND

Applications of biological and chemical sensors stimulate the demand and development of ultra-sensitive devices to detect bio-molecules with very low concentrations.

Micro-resonators sensor and photonic crystal sensor (PCs) have been proposed for sensing analytes at low level. These devices offer an advantage of reducing the device size by orders of magnitude without sacrificing the interaction length by virtue of their high quality-factor (Q) resonance. The resonance effect provides an equivalently long interaction length to achieve a sufficient phase shift. Such a property can dramatically reduce the device size and the amount of analytes needed for detection.

However, micro-resonator sensors still rely on evanescent wave sensing scheme which make it difficult to further reduce device size and the amount of analytes needed for detection. A high sensitive disk resonator has been demonstrated by A. M. Armani et al. ("Label-free, Single-molecule Detection with Optical Microcavities", Science, Vol. 317, pp.783-787) for single molecule detection by improving Q value. However, to achieve the ultra-high Q value, the disk edge has to be melt by laser to form a smooth and stress-free surface. Such a process is difficult to control and not suitable for mass production.

Photonic crystals, unlike many sensing platforms that utilize the interaction between the small evanescent tail of the electromagnetic field and the analyte, confine a high electric field in the small modal volumes and provide efficient light-matter interaction with minuscule volumes of analyte. However, to improve the confinement, the index contrast has to be increased. Then the geometrical features not only become very small but have to be very accurately fabricated. This results in significant challenge in fabrication of PC sensors.

It is an object of the present invention to provide a high sensitive optical resonator which is easy to be fabricated at low cost.

SUMMARY

An embodiment of the invention relates to an optical resonator. The optical resonator includes an input optical waveguide and a closed loop coupled to the input optical waveguide. The closed loop is adapted to receive light from the input optical waveguide, wherein the closed loop includes at least one hole formed within a portion of the closed loop.

Another embodiment of the invention relates to an optical sensing system including a source of light and at least one optical resonator. The optical resonator includes an input optical waveguide adapted to guide light received from the source of light, and a closed loop coupled to the input optical waveguide. The closed loop is adapted to receive light from the input optical waveguide wherein the closed loop includes at least one hole formed within a potion of the closed loop. The optical sensing system further includes at least one detector coupled to the optical resonator to measure a parameter of the optical resonator responsive to interaction of an analyte with the optical resonator.

These aspects of the invention will be more fully understood in view of the following description, drawings and non-limiting examples.

DETAILED DESCRIPTION

Figure 1A:
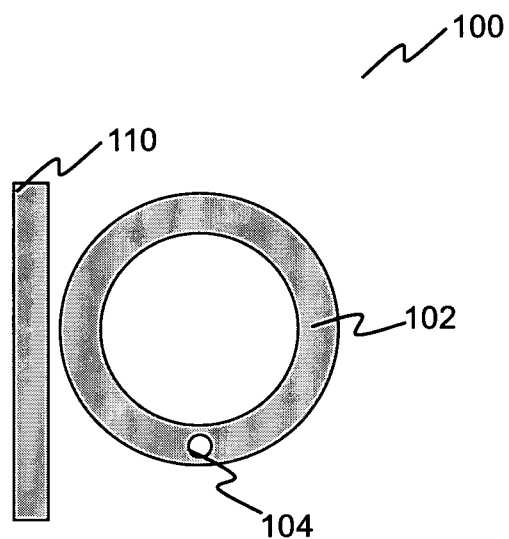
FIGS. 1A and 1B show optical resonators according to the embodiments of the invention.

Embodiments of the invention provide a high sensitive optical resonator and a high sensitive optical sensing system by using both evanescent wave sensing scheme and light-matter interaction sensing scheme. The high sensitive optical resonator according to the embodiment of the invention may be used in other applications, such as tunable modulators, tunable multiplexers and strain sensors.

An embodiment of the invention relates to an optical resonator. The optical resonator includes an input optical waveguide and a closed loop coupled to the input optical waveguide. The closed loop is adapted to receive light from the input optical waveguide, wherein the closed loop includes at least one hole formed within a portion of the closed loop.

The input optical waveguide may be adapted to receive light from a source of light. In an embodiment, the input optical waveguide may be a straight waveguide or a curved waveguide, guiding the light in a predetermined direction. The input optical waveguide may be fabricated on a substrate as planar optical waveguides, and may be used in integrated optical devices where optical elements, opto-electronic elements, or MEMS elements are integrated on one or more substrates.

The closed loop in this context may be embodied in any suitable form. In an embodiment, the closed loop is embodied by a microring, a microdisk, or a microsphere. The microring, microdisk or microsphere may have a circular or elliptical cross-section, for example. The closed loop may be embodied by a loop with arbitrarily curved circumference in other embodiments. Such a closed loop may be referred to as a closed loop waveguide, a closed loop resonator, or a microcavity resonator.

Light may be evanescently coupled from the input optical waveguide to the closed loop of the optical resonator. In an embodiment, the closed loop is adapted to receive light with a wavelength on resonance with the optical resonator from the input optical waveguide. In such a case, light with a wavelength off resonance with the optical resonator may not be coupled to the closed loop of the optical resonator.

In one embodiment, the input optical waveguide and the closed loop may each comprise a guiding layer, which may include any material which has suitable optical properties, such as Silicon, Silicon nitride, Silicon dioxide and polymer. In another embodiment, the input optical waveguide and the closed loop may be fabricated on top silicon layer of a silicon-on-insulator wafer such that the optical resonator may be integrated in a semiconductor chip.

The guiding layer of the input optical waveguide and the closed loop may be sandwiched in between a top and a bottom cladding layer. In an embodiment, the refractive index of the guiding layer is higher than the refractive index of the cladding layers, such that light can be confined within the guiding layer by so-called total internal reflection. Examples of the material that can be used in the cladding layers include air, water, polymer, silicon dioxide, silicon nitride, etc.

According to an embodiment, the dimension of the optical resonator depends on the refractive index contrast of materials that are used for the guiding layer and for the cladding layer. If the materials of high refractive index contrast are used, such as Si/air, the closed loop may have a radius in the order of microns. If the materials of low refractive index contrast are used, such as doped-SiO2/SiO2 or SiO2/polymer, the radius of the closed loop may be in the order of millimeter or centimeter in order to avoid high loss of light.

According to another embodiment of the invention, the waveguide width of the guiding layer of the closed loop also depends on the refractive index contrast of the materials that are used for the guiding layer and for the cladding layer. For example, if materials of high refractive index contrast are used, such as $Si/SiO_2$, the waveguide width of the guiding layer of the closed loop may be hundreds of nanometers. In another example, if materials of low refractive index contrast are used, such as doped-$SiO_2/SiO_2$ or $SiO_2$/polymer, the waveguide width of the guiding layer of the closed loop may be hundreds of micron.

In an embodiment of the invention, the at least one hole formed within the closed loop may be a hole penetrating through the closed loop, e.g. through the guiding layer of the closed loop. In an example wherein the guiding layer of the closed loop is sandwiched between the top cladding layer and the bottom cladding layer, the hole may also be formed to penetrate through the cladding layer like the top cladding layer, such that an analyte may be introduced into the hole. In another embodiment, the hole is formed as a partial through-hole, such as a trench at the surface of the closed loop. Depending on the application of the optical resonator, the depth of the hole may be adjusted. For example, a deeper hole may be formed in order to provide more space for interaction between light and analytes to be detected, thereby achieving higher sensitivity.

According to an embodiment, the at least one hole is adapted to be filled with a material having optical properties being different from those of an analyte to be detected. The optical properties may include but are not limited to any of the following properties: refractive index, absorption, and reflection coefficient. Here, the analyte to be detected may be gas, liquid, or biomolecules. In contrast to a conventional optical resonator wherein an analyte at the outer surface of the optical resonator only interacts with and affects a tail portion of light leaking from the optical resonator (referred to as the evanescent wave), the hole according to the embodiment of the invention is in the path of major portion of light and thus provides a direct light-matter interaction. As a result, the change in optical properties of the hole will have much bigger impact on the parameter of the optical resonator. For example, the hole may be adapted to be filled with air (n=1) or water (n=1.33), wherein n represents the refractive index. An analyte methanol (n=1.328) is adapted to flow in and mix with the filling material of air or water in the hole, thereby leading to a change in the parameter, e.g. the effective refractive index, of the hole. This will cause detectable change in the parameter, e.g. the spectral shift, of the optical resonator.

In another embodiment, the at least one hole is adapted to be filled with a material having optical properties being changeable in response to an interaction with an analyte to be detected. In an example, the material may include at least one capture element which is adapted to interact with the analyte, such that a specific analyte may be recognized. The at least one capture element may be selected from a group consisting of antibody, enzyme, nucleic acid, cell receptor, micro-organism. The capture element may also be a chemical substance in another embodiment. For example, if the analyte to be detected is a specific antigen, the capture element may be selected to be a corresponding antibody which specifically binds the antigen, thereby increasing the thickness of the filled material containing the capture element and thereby changing the optical properties of the hole. In another example when the analyte to be detected is gas or liquid, the material that will change its optical properties once interact with the gas or liquid may be filled in the at least one hole.

In a further embodiment, the at least one hole is adapted to be filled with a material that is adapted to decompose or evaporate in response to an interaction with an analyte to be detected. The decomposition or evaporation of the filled material results in a change in the effective optical properties of the hole, the detection of which results in the detection of the analyte. For example, the filled material may include a type of protein ABTNT (antibodies with specificity for TNT). When the analyte TNT (Trinitrotoluene) is provided in the hole, the TNT molecules interact with ABTNT (one protein) and cause it evaporating.

In accordance with the above embodiments, the at least one hole is adapted to be filled with a material with a suitable property, depending on the application of the optical resonator and the analyte to be detected. Examples of the material that may be filled in the hole according to the embodiments above include gas, liquid, inorganic and organic material, such as air, water and polymer.

In one embodiment, the at least one hole is adapted such that an analyte can be introduced into the hole. In one example, the analyte may be introduced into the hole by being contained in a gas or a fluid flowing through the optical resonator. In another example, the analyte is provided in the hole by inserting the analyte into the hole after forming the hole within the portion of the closed loop. In both examples, the analyte may be attached at the inner surface of the hole, or may be contained in the hole not in contact with the inner surface of the hole. The analyte provided in the hole interacts with light propagating in the closed loop, such that even small amount of the analyte is able to cause the parameter change, e.g. the spectral shift, of the optical resonator. Thus, small amount of the analyte can be detected.

The at least one hole may provide a direct light-matter interaction for the light propagating in the closed loop resonator to interact with the analyte provided in the hole, thereby increasing the degree of change in the optical properties of the optical resonator. Accordingly, the sensitivity of the optical resonator is increased, which may be used to detect small amount of analyte provided in the hole.

In another embodiment, the optical resonator is also adapted to get into contact with an analyte at the outer surface of the optical resonator. For example, the analyte may be provided at the outer surface of the optical resonator, so as to interact with the tail of an evanescent wave to cause the parameter change, such as spectral shift, of the optical resonator. The analyte may be provided at the outer surface of both the input optical waveguide and the closed loop of the optical resonator. In an embodiment, the analyte is only provided at the outer surface of the closed loop in order to achieve higher sensitivity.

In a further embodiment, the optical resonator is adapted to be provided with the analyte both in the hole and at the outer surface of the optical resonator as described above. This would increase the sensitivity and robustness of the optical resonator.

In an embodiment, at least one capture element is provided at the inner surface of the hole and/or at the outer surface of the optical resonator to interact with an analyte provided in the hole and/or in a surrounding area of the optical resonator, such that a specific analyte may be recognized. In an example, the analyte may be provided in a fluid flowing through the hole and/or the outer surface of the optical resonator. Here, the outer surface of the optical resonator refers to the outer surface of the closed loop and/or the outer surface of the input optical waveguide, similar to the embodiments described above. The at least one capture element may be selected from a group consisting of antibody, enzyme, nucleic acid, cell receptor, micro-organism. The capture element may also be chemical substance in another embodiment.

The at least one hole may be in any suitable configuration, such as a sphere, an ellipsoid, a cylinder, a cuboid, or irregular shape.

In an embodiment, the closed loop may include a plurality of holes. In one example, the one or more holes may be arranged at any location along the microring waveguide. In another example, the one or more holes may be arranged along the diameter of the microdisk waveguide.

The at least one hole may have dimensions of the order of nanometers to microns, depending on the dimension of the optical resonator. In an embodiment when the closed loop is a microring waveguide, the diameter of the at least one hole may be any size smaller than two third of the waveguide width, e.g., half of the waveguide width.

In some embodiments of the invention, the optical resonator comprises biocompatible material, such as Si and $SiO_2$, and is therefore biocompatible and operable in aqueous environment. The optical resonator as described in the above embodiments may be used in a sensor. For example, it can be used in an optical sensor for detection of protein within biological samples without the labeling or separation. In other examples, the optical resonator may be used in an optical sensor for bacteria and virus detection, medical diagnostics, screening of chemical compounds in drug discovery, food safety, environment monitoring, etc.

In other embodiments, the optical resonator can be used in many fields other than an optical sensor. For example, by filling the hole of the optical resonator with functional material having optical properties which are changeable in response to an applied external field, e.g., electric field or stress, the optical resonator according to the embodiments of the invention can be used as a tunable modulator, a tunable multiplex, a strain sensor, etc.

Another embodiment of the invention relates to an optical sensing system including a source of light and at least one optical resonator. The at least one optical resonator includes an input optical waveguide adapted to guide light received from the source of light, and a closed loop coupled to the input optical waveguide. The closed loop is adapted to receive light from the input optical waveguide, wherein the closed loop includes at least one hole formed within a potion of the closed loop. The optical sensing system further includes at least one detector coupled to the optical resonator to measure a parameter of the optical resonator responsive to an interaction of an analyte with the optical resonator.

The source of light may be a laser, for example. The light may be coupled from the source of light into the input optical waveguide directly or through an optical fiber. In an embodiment, the input optical waveguide may be a straight waveguide or a curved waveguide, guiding the light in a predetermined direction. The input optical waveguide may be fabricated on a substrate as planar optical waveguides, and may be used in integrated optical devices where optical elements, opto-electronic elements, or MEMS elements are integrated on one or more substrates.

The closed loop of the optical resonator may also be referred to as the closed loop waveguide or the closed loop resonator in this context. In an embodiment, the closed loop is embodied by a microring, a microdisk, or a microsphere, which may have a circular or elliptical cross-section, for example. In another embodiment, the closed loop may be embodied by a loop with arbitrarily curved circumference.

In an embodiment, the optical sensing system is adapted to couple light with a wavelength on resonance with the optical resonator from the input optical waveguide to the closed loop. For example, the closed loop may be disposed substantially close to the input optical waveguide to allow optical coupling between the closed loop and the input optical waveguide.

The closed loop and the input optical waveguide may each comprise a guiding layer, which is sandwiched in between a top cladding layer and a bottom cladding layer. In an embodiment, the refractive index of the guiding layer is higher than the refractive index of the cladding layers, such that light can be confined within the guiding layer by so-called total internal reflection.

As described in the embodiments above, the dimension and the waveguide width of the closed loop depend on the refractive index contrast of materials that are used for the guiding layer of the closed loop and for the cladding layers. Similarly, the waveguide width of the input optical waveguide may also depend on the refractive index contrast of materials that are used for the guiding layer of the input optical waveguide and for the cladding layers.

As also described in the embodiments above, the depth of the at least one hole formed within the closed loop may be adjusted depending on, e.g. the desired sensitivity of the optical resonator.

According to an embodiment, the at least one hole is adapted to be filled with a material having optical properties being different from those of an analyte to be detected.

In another embodiment, the at least one hole is adapted to be filled with a material having optical properties being changeable in response to an interaction with an analyte to be detected.

In a further embodiment, the at least one hole is adapted to be filled with a material that is adapted to decompose or evaporate in response to an interaction with an analyte to be detected. The decomposition or evaporation of the filled material results in a change in the effective optical properties of the hole, the detection of which results in the detection of the analyte.

In one embodiment, the hole is adapted such that the analyte may be introduced into the hole. The at least one hole may provide a direct light-matter interaction for the light propagating in the closed loop resonator to interact with the analyte provided in the hole, such that even small amount of the analyte is able to cause the parameter change, e.g. the spectral shift, of the optical resonator. Accordingly, the optical sensing system having the optical resonator according to the embodiment of the invention is highly sensitive to small amount of analyte.

In another embodiment, the optical resonator is adapted to get into contact with the analyte provided at the outer surface of the optical resonator, so that the analyte may interact with the tail of an evanescent wave to cause the spectral shift of the optical resonator.

In an embodiment, at least one capture element is provided at the inner surface of the hole and/or at the outer surface of the optical resonator to interact with an analyte provided in the hole and/or in a surrounding area of the optical resonator, such that a specific analyte may be recognized. In an example, the analyte may be provided in a fluid flowing through the hole and/or the outer surface of the optical resonator. The capture element may be immobilized at the inner surface of the hole and/or at the outer surface of the optical resonator e.g. at the outer surface of the closed loop, to interact with the analyte received by the optical sensing system. The at least one capture element may be selected from a group consisting of antibody, enzyme, nucleic acid, cell receptor, micro-organism. The capture element may also be chemical substance in another embodiment.

The at least one hole may be in any suitable configuration, such as a sphere, an ellipsoid, a cylinder, a cuboid, or irregular shape. In one example, the one or more holes may be arranged at any location along the microring waveguide. In another example, the one or more holes may be arranged along the diameter of the microdisk.

The at least one hole may have dimensions of the order of nanometers to microns. In an embodiment, the closed loop is a microring waveguide having a waveguide width of hundreds of nanometers, and the diameter of the at least one hole may be any size smaller than two third of the waveguide width. For example, the diameter of the hole may be half of the waveguide width of the closed loop.

According to an embodiment, the parameter of the optical resonator that is measured by the detector may be a resonance frequency of the optical resonator, a phase of light output from the optical resonator, and/or an intensity of light output from the optical resonator. For example, when the analyte within the hole of the optical resonator interacts with the light propagating in the optical resonator, the optical property of the optical resonator may be changed, which may be reflected as a changed resonance frequency of the optical resonator.

In one embodiment, the detector may be a spectrometer to measure the resonance frequency of the optical resonator based on the wavelength or frequency of light output from the optical resonator. The detector being a spectrometer may be used to measure spectrum or intensity of light output from the optical resonator. In another embodiment, the detector may be a photo-detector which is adapted to measure the intensity of light output from the optical resonator.

In an embodiment, the optical resonator may further include an output optical waveguide. The output optical waveguide is coupled to the closed loop, and is adapted to receive output light from the closed loop. The output optical waveguide is also coupled to the detector, and is adapted to guide the output light to the detector. In one embodiment, the output optical waveguide may be coupled to the detector directly. In another embodiment, the output optical waveguide is coupled to the detector through a converter, which may convert one optical property to another optical property, e.g. to convert resonance frequency to light intensity.

The optical sensing system in accordance with an embodiment of the invention may further include a signal processor adapted to compare the measured parameter with a reference parameter. The measured parameter may be the measured resonance frequency, the measured light phase and/or the measured light intensity after the interaction between the optical resonator and the analyte as explained above. The reference parameter may be the reference resonance frequency of the optical resonator, the reference phase of light output from the optical resonator, and/or the reference intensity of light output from the optical resonator, without the interaction of the analyte with the optical resonator. Thus, the difference of the measured parameter from the reference parameter may be used to determine the presence of the analyte.

According to an embodiment, the reference parameter of the optical resonator may be measured without an analyte being provided to the optical resonator. For example, the analyte is not provided in the hole of the optical resonator, and/or not provided at the outer surface of the optical resonator, and/or not provided in the surrounding area of the optical resonator.

According to another embodiment, the optical sensing system may further include a reference unit. The reference unit may include a reference optical resonator, which further includes a reference input optical waveguide adapted to guide light received from the source of light and includes a reference closed loop coupled to the reference input optical waveguide. The reference closed loop is adapted to receive light from the reference input optical waveguide, and includes at least one hole formed within a portion of the reference closed loop. The reference unit may further include a reference detector coupled to the reference optical resonator to measure a reference parameter of the reference optical resonator. The reference parameter may be the reference resonance frequency of the reference optical resonator, the reference phase and/or the reference intensity of light output from the reference optical resonator.

In an embodiment, analytes are not provided to the reference optical resonator, in order to maintain a stable status of the reference optical resonator, thereby providing a stable reference parameter.

In another embodiment, the structure, material and size of the reference optical resonator and the reference detector may be identical to those of the optical resonator and the detector which are used to interact with and detect the analyte.

In a further embodiment, the reference detector may be a spectrometer adapted to measure spectrum or intensity of light output from the reference optical resonator, or may be a photo-detector adapted to measure the intensity of light output from the reference optical resonator.

The reference optical resonator may further include a reference output optical waveguide. The reference output optical waveguide is coupled to the reference closed loop to receive reference output light from the reference closed loop, and is also coupled to the reference detector to guide the reference output light to the reference detector. Similar to the embodiments as described above, the reference output optical waveguide may be coupled to the reference detector directly, or coupled to the reference detector through a converter adapted to convert one optical property to another optical property.

According to an embodiment, the number of the optical resonators and the number of the detectors may be equal to or above 2, respectively.

The plurality of optical resonators and the plurality of detectors may be grouped into a plurality of groups, wherein each group comprises one optical resonator and one detector. The optical resonator of a respective group is coupled to the detector belonging to the same group.

In one embodiment, the analyte is provided to the optical resonators of the plurality of groups, such that a plurality of measured parameters of the optical resonators may be obtained at the plurality of detectors in the plurality of groups. This may provide a robust and reliable optical sensing system which is capable of detecting the analyte even if some of the optical resonators do not interact with the analyte properly.

In another embodiment, the plurality of optical resonators in the plurality of groups may be provided with a plurality of types of analytes, which may be provided in the hole of the optical resonators, and/or at the outer surface of the optical resonators, and/or in the surrounding area of the optical resonators, as described in the embodiments above. In this embodiment, the plurality of types of analytes may interact with light waves to affect the optical property of the optical resonators in a different degree such that the optical sensing system may be used to sense or detect a plurality of types of analytes.

The optical sensing system as described in the above embodiments may be integrated in an optical chip. In such a way, a miniaturized and portable optical sensing system is provided for easy and convenient use.

The above embodiments of the invention provide a high sensitive optical sensing system, by using an optical resonator having at least one hole formed within a portion of the closed loop. This high sensitivity to small amount of analytes significantly reduces the amount of analytes that is needed to be used. The simple structure of the optical sensing system is also easy to be fabricated and integrated using the current semiconductor technology at low cost. For example, VLSI Si technology may be used to mass-fabricate a planar optical sensing system according to the embodiments of the invention.

Figure 1B:
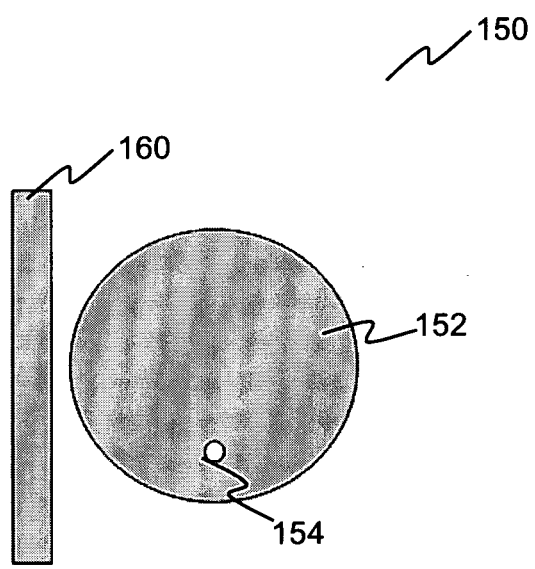

FIGS. 1A and 1B show optical resonators according to the embodiments of the invention.

In FIG. 1A, an optical resonator 100 includes an input optical waveguide 110 and a closed loop 102 coupled to the input optical waveguide 110. The closed loop 102 is adapted to receive light from the input optical waveguide 110, and includes at least one hole 104 formed within a portion of the closed loop 102.

Here, the closed loop 102 is embodied by a microring having a circular cross-section as shown in FIG. 1A. The closed loop 102 may have an elliptical cross-section in another embodiment. The dimension of the closed loop 102 and the waveguide width of the closed loop 102 depend on the refractive index contrast of the material used for closed loop 102 and cladding layers, as described in the embodiments above. For example, if Si is used in the closed loop 102 and SiO2 is used for cladding layers, the radius of the closed loop 102 may be in the order of microns, e.g., 5 μm, and the waveguide width of the closed loop 102 may be hundreds of nanometers, e.g., 500 nm.

In one embodiment, the closed loop 102 and input optical waveguide 110 may comprise materials such as Si, SiO2, SiN, polymer, etc. In another embodiment, the input optical waveguide 110 and the closed loop 102 may be sandwiched in between a top cladding layer and a bottom cladding layer (not shown in FIG. 1A). The refractive index of the input optical waveguide 110 and the closed loop 102 is higher than the refractive index of the cladding layers, such that light can be confined within the guiding layer by so-called total internal reflection. The input optical waveguide 110 and the closed loop 102 may be fabricated on top Si layer of a silicon-on-insulator wafer such that the micro-resonator 100 may be integrated in a semiconductor chip.

The at least one hole 104 may be a hole penetrating through the closed loop 102, or a partial through-hole at the surface of the closed loop 102. Depending on the application of the optical resonator 100, the depth of the hole 104 may be adjusted to achieve different degree of sensitivity.

Similar to the embodiments above, the at least one hole 104 may be adapted to be filled with a material having optical properties being different from those of an analyte to be detected, or a material having optical properties being changeable in response to an interaction with an analyte to be detected, or a material that is adapted to decompose or evaporate in response to an interaction with an analyte to be detected. The hole 104 may provide a direct light-matter interaction for the light propagating in the closed loop 102 of the optical resonator 100, thereby increasing the degree of change in the optical property of the optical resonator 100 to provide a high sensitive optical resonator.

In one embodiment, an analyte may be provided within the hole 104. By providing the analyte in the hole 104, the sensitivity of the optical resonator 100 may be highly increased.

The hole 104 may be in any suitable configuration, such as a sphere or a cylinder, and can be arranged at any location along the closed loop 102 as shown in FIG. 1A. The diameter of the hole 104 may be any size smaller than two third of the waveguide width, e.g., half of the waveguide width of the microring 102.

FIG. 1B shows an optical resonator 150 according to another embodiment of the invention, wherein the optical resonator 150 includes an input optical waveguide 160 and a closed loop 152 coupled to the input optical waveguide 160. The closed loop 152 is adapted to receive light from the input optical waveguide 160, and includes a hole 154 formed within a portion of the closed loop 152.

In this embodiment, the closed loop 152 is embodied by a microdisk having a circular cross-section as shown in FIG. 1B. The closed loop 152 may have an elliptical cross-section in another embodiment. The radius of the closed loop 152 may range from the order of microns to the order of centimeters depending on the material contained in the closed loop 152.

In an embodiment, the waveguide 160 and closed loop 152 may be sandwiched in between a cladding layer. The refractive index of the waveguide 160 and closed loop 152 is higher than the refractive index of the cladding layer in order to confine light within the guiding layer.

The hole 154 may be adapted to be filled with similar materials as the hole 104 described in the above embodiments, to provide a direct light-matter interaction for the light propagating in the closed loop 152 of the optical resonator 150. Similar to the embodiments as explained above, the hole 154 may be provided with an analyte.

The hole 154 may be of any suitable configuration, such as a sphere or a cylinder, and can be arranged at any location along the closed loop 152 as shown in FIG. 1B.

Figure 2:
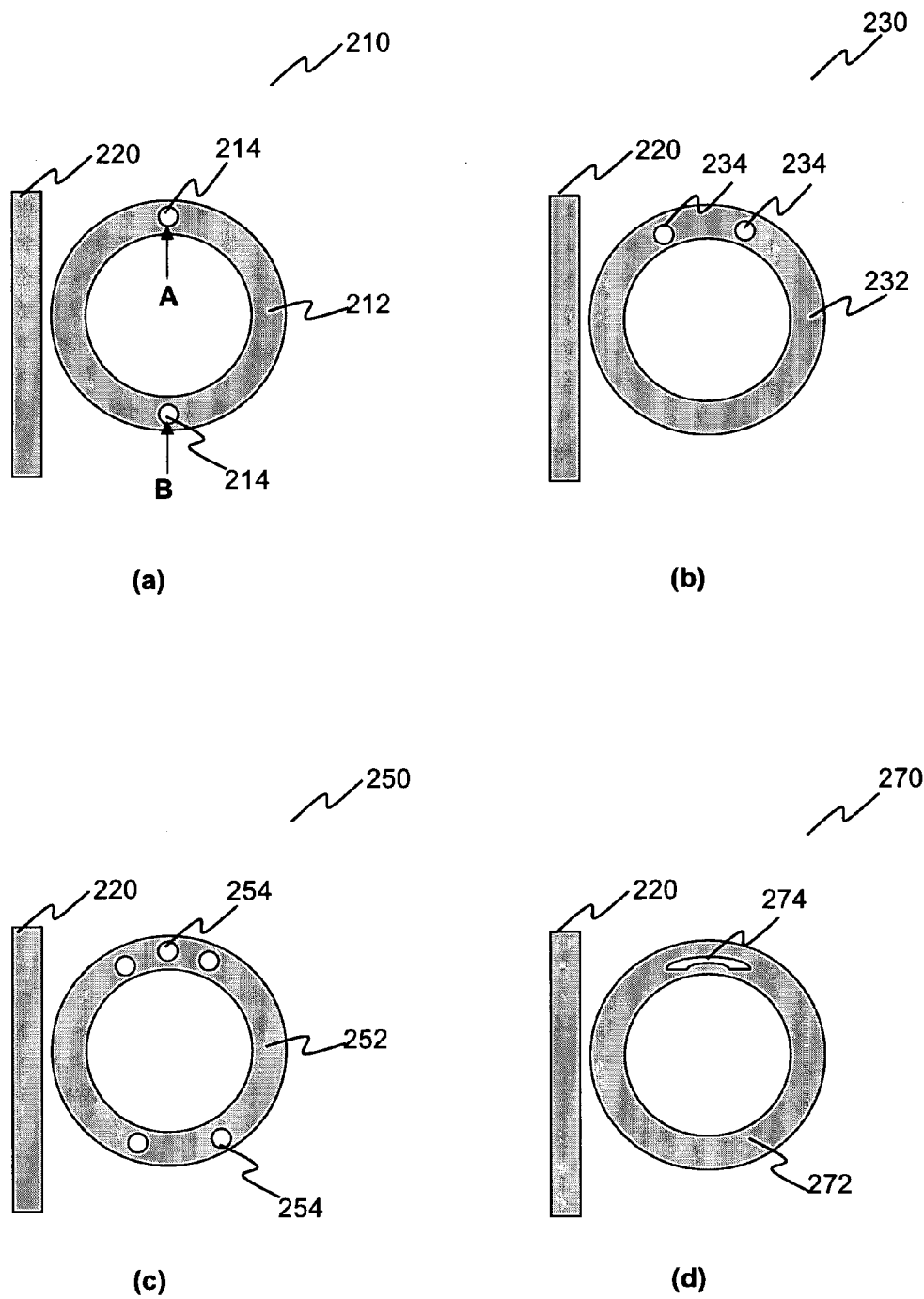
FIG. 2 shows the optical resonators according to a plurality of the embodiments of the invention.

FIG. 2 shows the optical resonators according to a plurality of the embodiments of the invention.

The optical resonators 210, 230, 250 and 270 as shown in FIG. 2(a)-(d) respectively include an input optical waveguide 220 and a closed loop 212, 232, 252 and 272 coupled to the input optical waveguide 220. The closed loops 212, 232, 252 and 272 are adapted to receive light from the input optical waveguide 220, for example, to receive light with a wavelength on resonance with the optical resonators 210, 230, 250 and 270.

The closed loops 212, 232, 252 and 272 are embodied as a microring. Each closed loop 212, 232, 252 and 272 includes at least one hole 214, 234, 254 and 274 formed within the closed loop 212, 232, 252 and 272. The holes 214, 234, 254 and 274 may have different configuration and arrangement according to the embodiments in the following.

In FIG. 2(a), the closed loop 212, being a microring waveguide, includes two holes 214 which are sphere or cylinder holes. The holes 214 are arranged within the microring waveguide and along a diameter of the microring 212, for example, at the position A and B in FIG. 2(a), wherein A and B are two end points of the diameter of the microring. The optical resonator 210 having the holes 214 located at position A or B of the closed loop 212 may have an increased sensitivity in detecting analytes, if the optical resonator 210 is used as an optical sensor. Thus, even small amount of analytes may be detected using the optical resonator 210.

In FIG. 2(b), the closed loop 232 includes two holes 234 in sphere or cylinder shape. The holes 234 are arranged within the microring waveguide 232, and are arranged with a small distance between each other, as shown in FIG. 2(b).

FIG. 2(c) shows a plurality of holes 254, in this example five holes 254, arranged within the microring waveguide 252. The holes 254 may be distributed at two ends of a diameter of the microring 252 as shown in FIG. 2(c).

FIG. 2(d) shows the optical resonator 270 in another embodiment of the invention, wherein a hole 274 in an elongated shape is formed within the closed loop 272.

Figure 3:
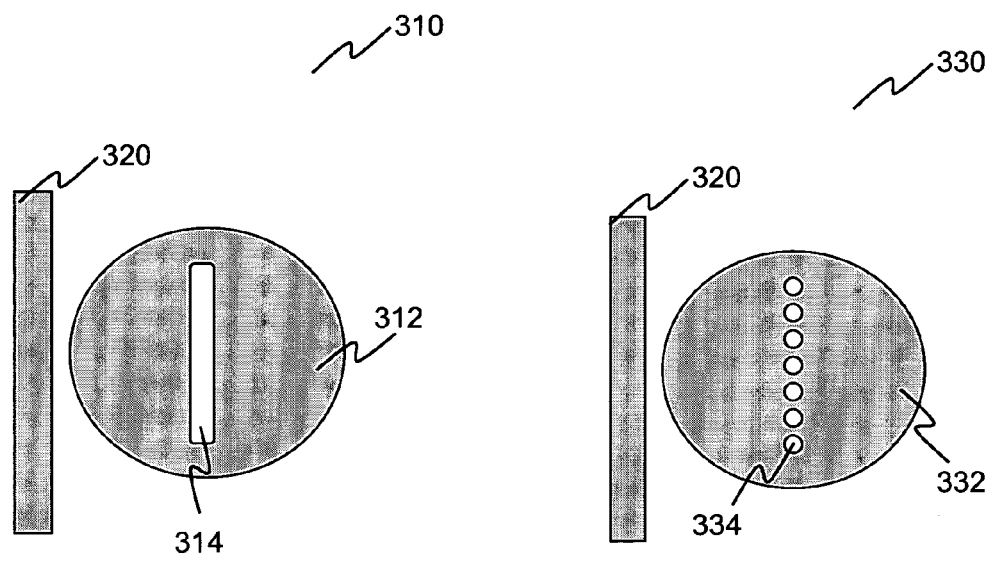
FIG. 3 shows further embodiments of the optical resonators according to the invention.
Figure 3:
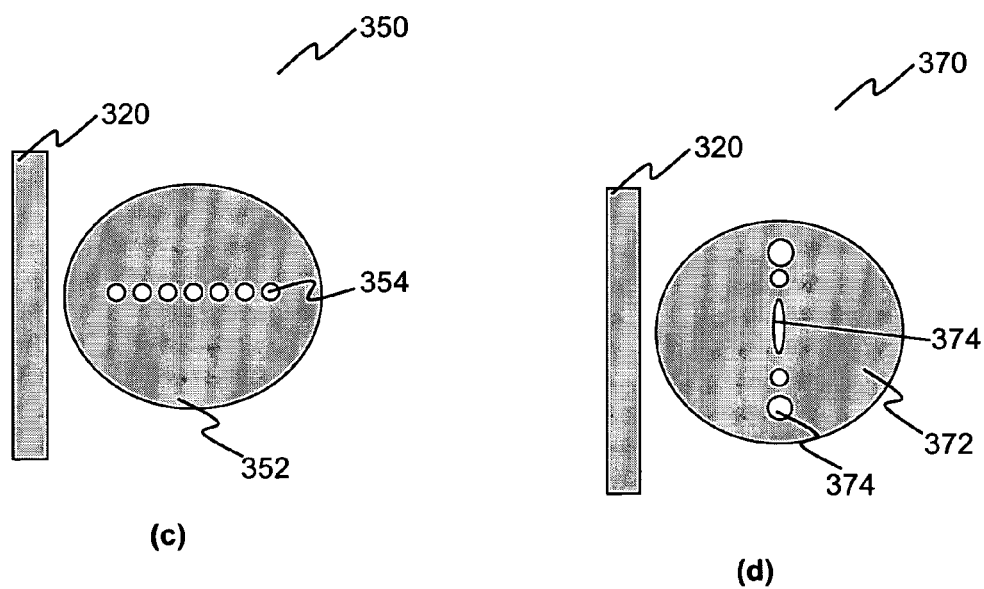

FIG. 3 shows further embodiments of the optical resonators according to the invention.

The optical resonators 310, 330, 350 and 370 as shown in FIG. 3(a)-(d) respectively include an input optical waveguide 320 and a closed loop 312, 332, 352 and 372 coupled to the input optical waveguide 320. The closed loops 312, 332, 352 and 372 are adapted to receive light from the input optical waveguide 320, for example, to receive light with a wavelength on resonance with the optical resonators 310, 330, 350 and 370.

The closed loops 312, 332, 352 and 372 are embodied as a microdisk having a circular or elliptical cross-section. Each closed loop 312, 332, 352 and 372 includes at least one hole 314, 334, 354 and 374 formed within the closed loop 312, 332, 352 and 372. The holes 314, 334, 354 and 374 may have different configurations and arrangements as will be explained in the following.

In FIG. 3(a), the closed loop 312, being a microdisk, includes a cuboid hole 314. The hole 314 is arranged within the microdisk 312 and along a diameter of the microdisk 312. Here, for example, the cuboid hole 314 is arranged to be in a direction parallel to the input optical waveguide 320. In other examples, the cuboid hole 314 may be arranged in other directions as well.

In FIG. 3(b), the closed loop 332 includes a plurality of holes 334 in sphere or cylinder shape. The holes 334 are arranged within the microdisk 332, and are arranged in a line along a diameter of the microdisk 332, as shown in FIG. 3(b).

FIG. 3(c) shows a plurality of holes 354 arranged within the microdisk 352. The plurality of holes 354 are arranged in a line along a diameter of the microdisk 352, but in a direction perpendicular to that of FIG. 3(b). In other examples, the plurality of holes 354 may be arranged in other directions as well.

FIG. 3(d) shows the optical resonator 370 in another embodiment of the invention, wherein a plurality of holes 374 in different shape and size are formed within the closed loop 372. The plurality of holes 374 include sphere, cylinder and ellipsoid holes 374, and may be arranged in a line along the diameter of the microdisk 370.

The configuration and arrangement of the at least one hole within the closed loop as described in the above embodiments of FIGS. 1-3 may provide different degrees of improvement to the sensitivity of the optical sensor using the optical resonators of FIGS. 1-3.

Here, the input optical waveguide 110, 160, 220, 320 is a straight optical fiber as shown in FIGS. 1-3. It is noted that the input optical waveguide used to couple light to the optical resonator can be curved along a portion of the closed loop of the optical resonators in accordance with other embodiments of the invention.

Figure 4A:
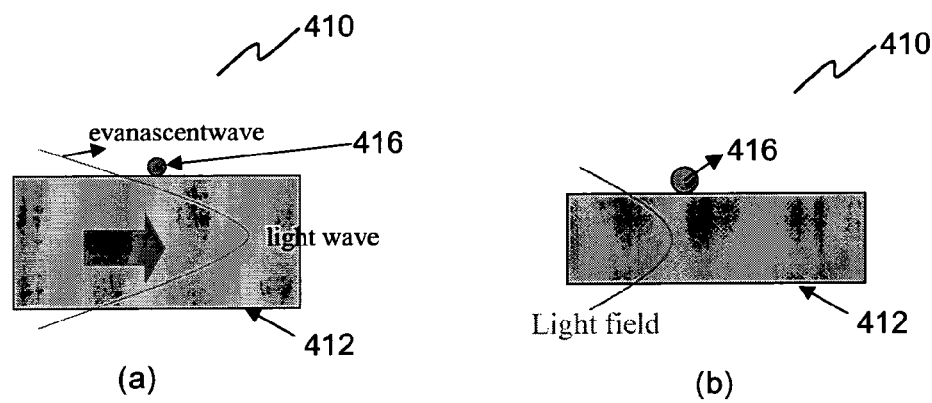
FIG. 4A shows the top view and cross-sectional view of a conventional optical resonator.

FIG. 4A shows the top view and cross-sectional view of a conventional optical resonator.

FIGS. 4A (a) and (b) show the top view and the cross-sectional view of a conventional optical resonator 410, respectively. The conventional optical resonator 410 includes a closed loop 412, wherein light wave coupled from an input optical waveguide (not shown) is propagating within the closed loop 412. An analyte 416 is usually provided at the surface of the closed loop 412 or in the surrounding area of the closed loop 412, and the analyte 416 only interacts with and affect the tail part of evanescent wave.

Figure 4B:
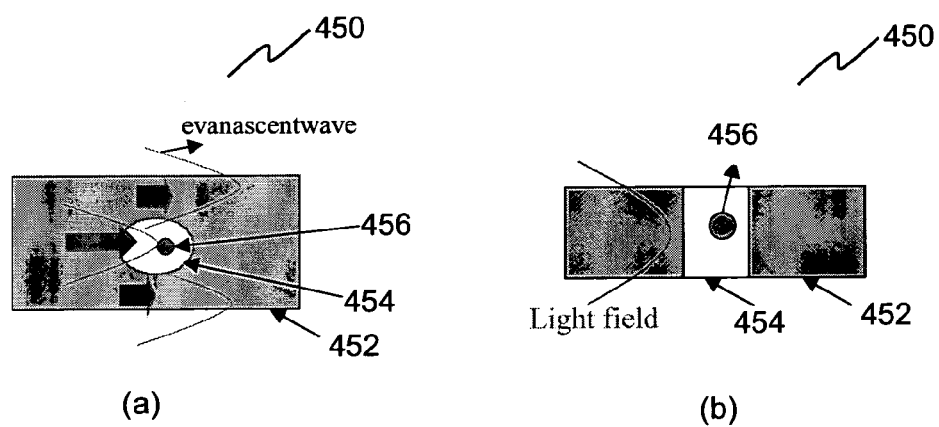
FIG. 4B shows the top view and cross-sectional view of an optical resonator according to an embodiment of the invention.

FIG. 4B shows the top view and cross-section view of an optical resonator according to an embodiment of the invention.

FIGS. 4B (a) and (b) show the top view and the cross-sectional view of an optical resonator 450 according to the embodiment of the invention, respectively. The optical resonator 450 according to the embodiment of the invention includes a closed loop 452, wherein within a portion of the closed loop 452 a hole 454 is formed. An analyte 456 is provided in the hole 454 being in the light path, such that the analyte 456 directly interacts with both evanescent wave and light wave to provide higher degree of change in optical properties of the optical resonator 450. In this way, the optical resonator 450 having a high sensitivity to analyte is achieved. The analyte can also be provided at the outer surface or the surrounding area of the optical resonator 450 similar to the location of the analyte 416 in FIG. 4A, but can be detected with lower sensitivity compared to the analyte 456 provided in the hole 454 of the optical resonator 450.

Figure 5A:
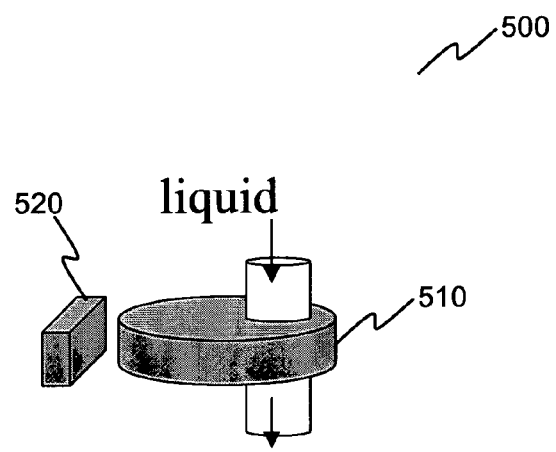
FIGS. 5A and 5B show the optical resonator according to the embodiments of the invention.
Figure 5B:
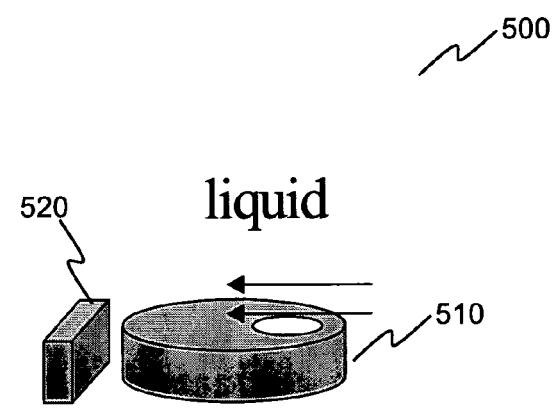

FIGS. 5A and 5B show the optical resonator according to the embodiments of the invention.

As shown in FIGS. 5A and 5B, an optical resonator 500 includes an input optical waveguide 520 and a closed loop 510 coupled to the input optical waveguide 520. The closed loop 510 is adapted to receive light from the input optical waveguide 520. In this embodiment the closed loop 510 is embodied by a microdisk. The closed loop 510 also includes a hole, in this embodiment a cylinder hole, formed within a portion of the closed loop 510.

As described in the embodiments above, the analyte may be provided in the hole of the closed loop 510, so as to interact with both evanescent wave and light wave to increase the sensitivity of the optical resonator 500.

In an embodiment as shown in FIG. 5A, the analyte is provided in the hole by being provided in the fluid flowing through the hole. The fluid is adapted to directly flow into the hole in a vertical direction relative to the closed loop 510. In this embodiment, the analyte is provided in the hole of the closed loop, being either attached to the inner surface of the hole or contained within the hole not in contact with the inner surface of the hole.

In another embodiment as shown in FIG. 5B, the analyte is provided in the hole as well as at the outer surface of the optical resonator by being provided in the fluid flowing over the optical resonator 500. The fluid is adapted to flow over the closed loop 510 of the optical resonator 500 and the hole therein in a lateral direction of the closed loop 510.

The above embodiments in FIGS. 5A and 5B for providing an analyte may be used in the application that the analyte to be detected is particles in the fluid or is the fluid itself. In other applications where the optical resonator 500 is used to detect specific analytes, capture elements as explained in the embodiments above may also be provided in the hole and/or at the outer surface of the closed loop 510. The capture elements are used to improve the optical resonator's specificity to the analytes to be detected, since false signal induced by non-specific adsorption of analytes can be minimized.

Figure 6:
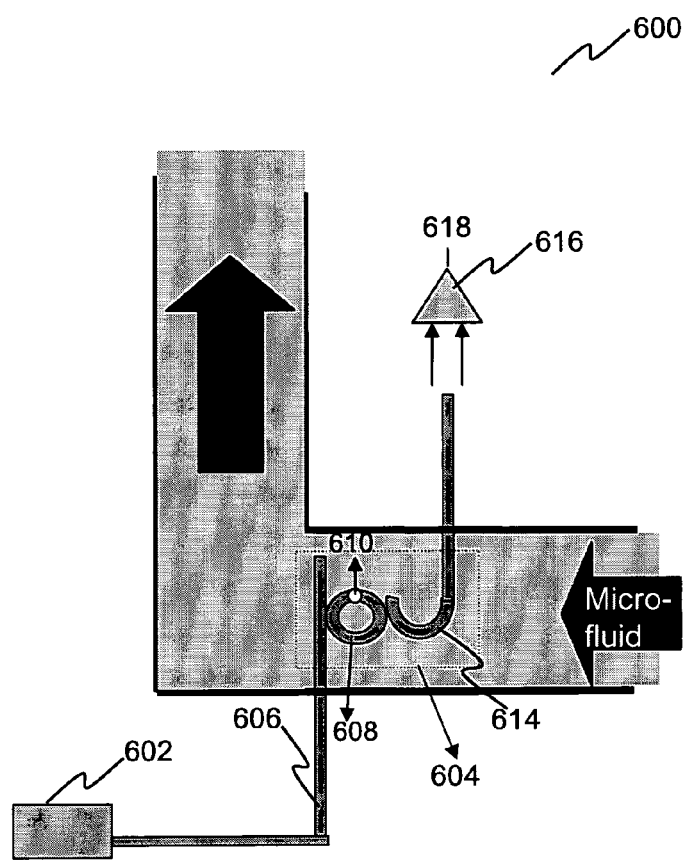
FIG. 6 shows an optical sensing system according to an embodiment of the invention.

FIG. 6 shows an optical sensing system according to an embodiment of the invention, wherein the optical resonators described in the above embodiments may be used.

The optical sensing system 600 includes a source of light 602, and at least one optical resonator 604. The optical resonator 604 includes an input optical waveguide 606 and a closed loop 608 coupled to the input optical waveguide 606. The closed loop 608 is adapted to receive light from the input optical waveguide 606, and includes at least one hole 610 formed within a portion of the closed loop 608. The optical sensing system 600 further includes at least one detector 616, coupled to the optical resonator 604 to measure a parameter of the optical resonator 604 responsive to interaction of an analyte with the optical resonator 604.

The source of light 602 may be a laser, for example, which may provide light with a range of wavelengths. The light may be coupled to the input optical waveguide 606 through a fiber (not shown).

The optical sensing system 600 is adapted to couple light with a wavelength on resonance with the optical resonator 604 from the input optical waveguide 606 to the closed loop 608. In an embodiment, the closed loop 608 may be disposed substantially close to the input optical waveguide 606 to allow optical coupling between the closed loop 604 and the input optical waveguide 606.

The optical resonator 604 may be the optical resonator described in the above embodiments. In this embodiment, the closed loop 608 of the optical resonator 604 is a microring having a circular cross-section, and the hole 610 is a cylinder hole as shown in FIG. 6. It is noted that the configuration and arrangement of the closed loop 608 and the hole 610 may be different in other embodiments, such as the embodiments as shown in FIGS. 1-3, to cater for different scenario of application and fabrication requirements.

The hole 610 may be filled with a material having specific optical properties or being changeable in its physical state, as explained in the embodiments above.

In one embodiment, the analyte may be provided in the hole 610 by being provided in the fluid flowing through the optical resonator 604 and the hole 610, as shown in FIG. 6. The analyte in the hole 610 interacts with light wave and evanescent wave so as to cause the parameter change, e.g. the spectral shift of the optical resonator 604. In another embodiment, capture element may also be provided in the hole 610, e.g., being immobilized along the circumference of the hole 610, to interact with and recognize specific analyte received by the optical sensing system 600.

The at least one capture element may be selected from a group consisting of antibody, enzyme, nucleic acid, cell receptor, micro-organism. The capture element may also be chemical substance in another embodiment. In one example when the analyte is a specific antigen, the capture element may be selected to be a corresponding antibody which specifically binds the antigen so as to affect the optical property of the optical resonator 604.

The detector 616 is coupled to the optical resonator 604 to measure the parameter, e.g., the resonance frequency, light intensity or light phase of the optical resonator 604. The change of the optical property of the optical resonator 604 caused by the interaction between the analyte and the optical resonator 604 may be reflected as a changed parameter of the optical resonator 604. The detector 616 may be a spectrometer which is capable of measuring both spectrum and intensity. In another embodiment as will be explained below, the detector 616 may be an intensity sensitive photodetector, which is coupled to the optical resonator 606 through a converter converting frequency parameter of the optical resonator 606 to intensity parameter.

In an embodiment, the optical resonator 604 may further include an output optical waveguide 614. The output optical waveguide 614 is coupled to the closed loop 608 at one end, and is adapted to receive output light from the closed loop 608. The output optical waveguide 614 is also coupled to the detector 616 at the other end, and is adapted to guide the output light to the detector 616. The output optical waveguide 614 may be coupled to the detector 616 directly, or through a converter as will be described below. The output optical waveguide 614 may be a straight waveguide or a curved waveguide in order to output the light in any desired direction.

The output sensing signal 618 of the detector 616 will be analyzed or may be further processed for analysis. For example, a signal processor (not shown) may be provided to compare the output sensing signal 618 with a reference signal to determine the change of the optical property of the optical resonator 604, thereby determining the existence of the analyte. The reference signal may be provided, e.g., through the same detector 616, when the fluid containing the analyte is not provided to the optical resonator 604.

Figure 7:
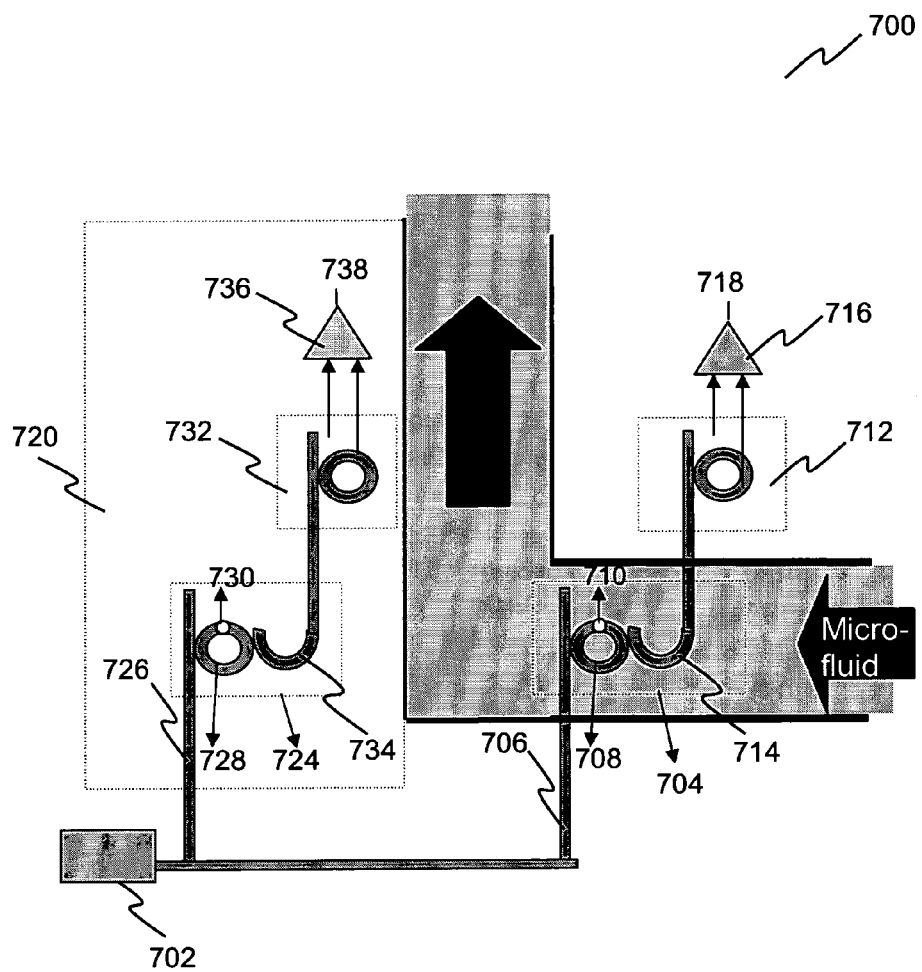
FIG. 7 shows an optical sensing system according to an embodiment of the invention.

FIG. 7 shows an optical sensing system according to another embodiment.

The optical sensing system 700 includes a source of light 702, an optical resonator 704, and a detector 716 coupled to the optical resonator 704, similar to the optical sensing system 600 of FIG. 6. Similar to the embodiment of FIG. 6, the optical resonator 704 includes an input optical waveguide 706 and a closed loop 708 coupled to the input optical waveguide 706. The closed loop 708 is adapted to receive light from the input optical waveguide 706, and includes at least one hole 710 formed within a portion of the closed loop 708. The detector 716 is adapted to measure a parameter of the optical resonator 704 responsive to interaction of an analyte with the optical resonator 704.

The optical sensing system 700 further includes a reference unit 720. The reference unit 720 includes a reference optical resonator 724, which further includes a reference input optical waveguide 726 and a reference closed loop 728 which is coupled to the reference input optical waveguide 726 and which is adapted to receive light from the reference input optical waveguide 726. The closed loop 728 may include at least one hole 730 formed within a potion of the closed loop 728. The reference unit 720 may further include a reference detector 736 coupled to the reference optical resonator 724 to measure a reference parameter of the reference optical resonator 724. The reference parameter may be the reference resonance frequency, the reference light intensity or the reference light phase of the reference optical resonator 724. In this embodiment, fluid containing the analyte is not provided to the reference optical resonator 724 in order to measure the reference parameter without the interaction with the analyte.

In this embodiment, the detector 716 is coupled to the optical resonator 704 through a converter 712. The converter 712 may be a microring resonator to convert frequency parameter to intensity parameter. In this way, the detector 716 may be selected as an intensity sensitive photo-detector to measure the intensity change of the light output from the optical resonator 704.

Similarly, the reference detector 736 is coupled to the reference optical resonator 724 through a reference converter 732. The reference converter 732 is a microring resonator to convert frequency change to intensity change. In this way, the reference detector 736 is selected as an intensity sensitive photo-detector or spectrometer to measure the reference intensity of the light output from the reference optical resonator 724.

In other embodiments, the detector 716 and the reference detector 736 may be coupled directly to the optical resonator 704 and the reference optical resonator 724, respectively. In this embodiment, the detector 716 and the reference detector 736 may be selected as a spectrometer to measure the frequency of the optical resonator 704 and the reference optical resonator 724, respectively.

In an embodiment, the reference optical resonator 724 may further include a reference output optical waveguide 734. The reference output optical waveguide 734 is coupled to the reference closed loop 728 at one end, and is adapted to receive output light from the reference closed loop 728. The reference output optical waveguide 734 is also coupled directly or through the reference converter 732 to the reference detector 736 at the other end, and is adapted to guide the output light to the reference detector 736.

The output reference signal 738 of the reference detector 736 may be analyzed or further processed through a signal processor (not shown). For example, the signal processor may be used to compare an output sensing signal 718 of the detector 716 with the reference signal 738 to determine the change of the optical property of the optical resonator 704, thereby determining the existence of the analyte.

The structure, material and size of the reference optical resonator 724 and the reference detector 736 may be identical to those of the optical resonator 704 and the detector 716 which are used to interact with and detect the analyte.

Figure 8:
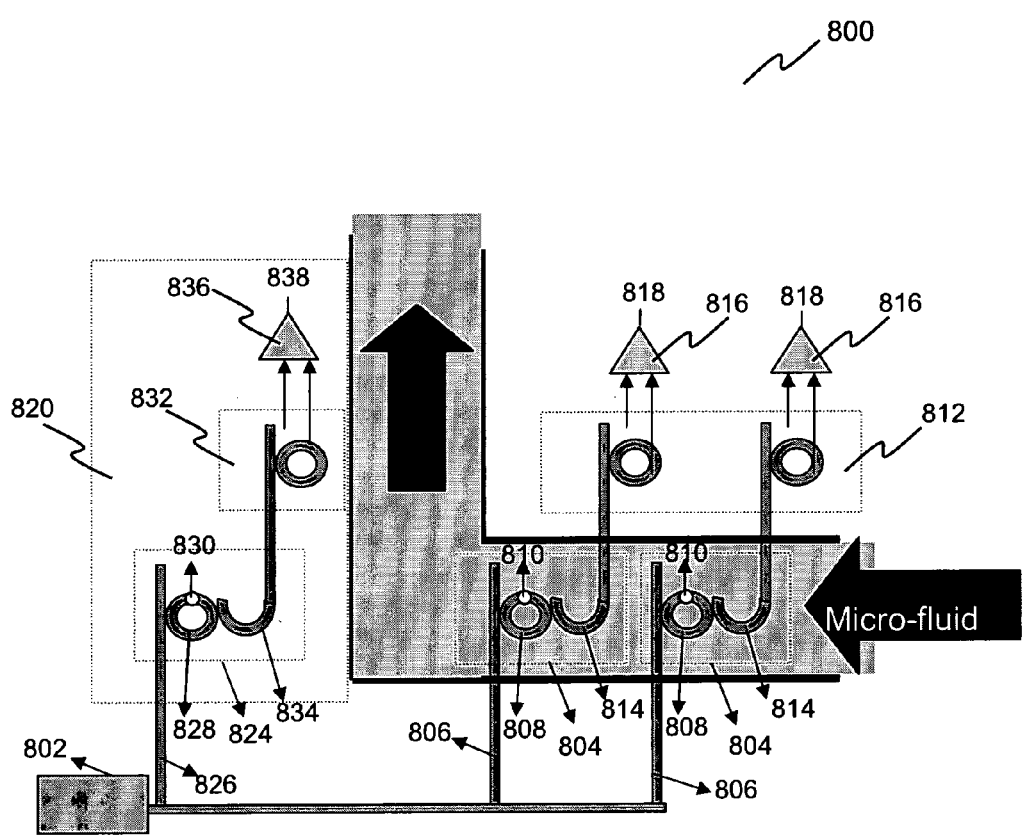
FIG. 8 shows an optical sensing system according to an embodiment of the invention.

FIG. 8 shows an optical sensing system according to another embodiment of the invention.

The optical sensing system 800 is similar to the optical sensing system 600 and 700 of FIGS. 6 and 7, and includes a source of light 802, optical resonators 804, detectors 816, and reference unit 820.

In optical sensing system 800, the number of the optical resonators 804 and the number of the detectors 816 may be equal to or above 2, respectively, wherein only two optical resonators 804 and two detectors 816 are shown in FIG. 8.

The plurality of optical resonators 804 and the plurality of detectors 816 are grouped into a plurality of groups, wherein each group comprises one optical resonator 804 and one detector 816. The optical resonator 804 of a respective group is coupled to the detector 816 belonging to the same group. Each of the optical resonators 804 includes an input optical waveguide 806 and a closed loop 808 coupled to the input optical waveguide 806, wherein the closed loop 808 includes a hole formed within the closed loop 808.

In one embodiment, the fluid containing the analyte is adapted to flow through the optical resonators 804 of the plurality of groups, such that a plurality of measured parameter of the optical resonators 804 may be obtained at the plurality of detectors 816 in the plurality of groups. This may provide a robust and reliable optical sensing system which is capable of detecting the analyte even if some of the optical resonators 804 do not interact with the analyte properly. The plurality of measured parameter 818 of the optical resonators 804 may be further processed through a signal processor.

The detectors 816 are coupled to the optical resonators 804 through converters 812, which are microring resonators to convert frequency change of the optical resonators 806 to intensity change. In this way, the detectors 816 may be selected as intensity sensitive photo-detectors to measure the intensity change of the light output from the optical resonators 804. In other embodiments, the detectors 816 may be coupled to the optical resonators 804 directly as shown in FIG. 6 above.

A plurality of output optical waveguides 814 may be provided in the plurality of optical resonators 804 in the plurality of groups. The plurality of output optical waveguides 814 is coupled to the plurality of closed loops 808 at one end, and is coupled, directly or through the plurality of converters 812, to the plurality of detectors 816 at the other end, as described in the embodiments above.

In another embodiment, the plurality of optical resonators 804 in the plurality of groups may be provided with a plurality of types of analytes. The plurality of types of analytes may interact with the optical resonators 804 and affect the optical properties of the respective optical resonators 804 in a different degree, such that the optical sensing system 800 may be used to sense or detect a plurality of types of analytes.

The reference unit 820 is similar to the reference unit 720 of FIG. 7, and includes a reference optical resonator 824, a reference converter 832 and a reference detector 836. The reference optical resonator 824 includes a reference input optical waveguide 826 and a reference closed loop 828, wherein the reference closed loop 828 include a hole 830 formed within a portion of the reference closed loop 828. The reference optical resonator 824 may also include a reference output optical waveguide 834 to guide the output reference light of the reference optical resonator 824 to the reference detector 836. The reference output 838 of the reference detector 836 may be further processed by other electronics circuits.

The optical sensing systems 600, 700, 800 as described in the above embodiments may be integrated in an optical chip, respectively. For example, the respective components of the optical sensing systems 600, 700, 800, may be respectively fabricated on a silicon-on-insulator wafer using the semiconductor technology. In such a way, an autonomous, miniaturized and portable optical sensing system is provided for easy and convenient use.

The above embodiments of the invention provides a high sensitive optical sensing system, by using a optical resonator having at least one hole formed within a portion of the closed loop. This high sensitivity to small amount of analytes significantly reduces the amount of analytes that is needed to be used. The simple structure of the optical sensing system is also easy to be fabricated and integrated using the current semiconductor technology at low cost.

Figure 9:
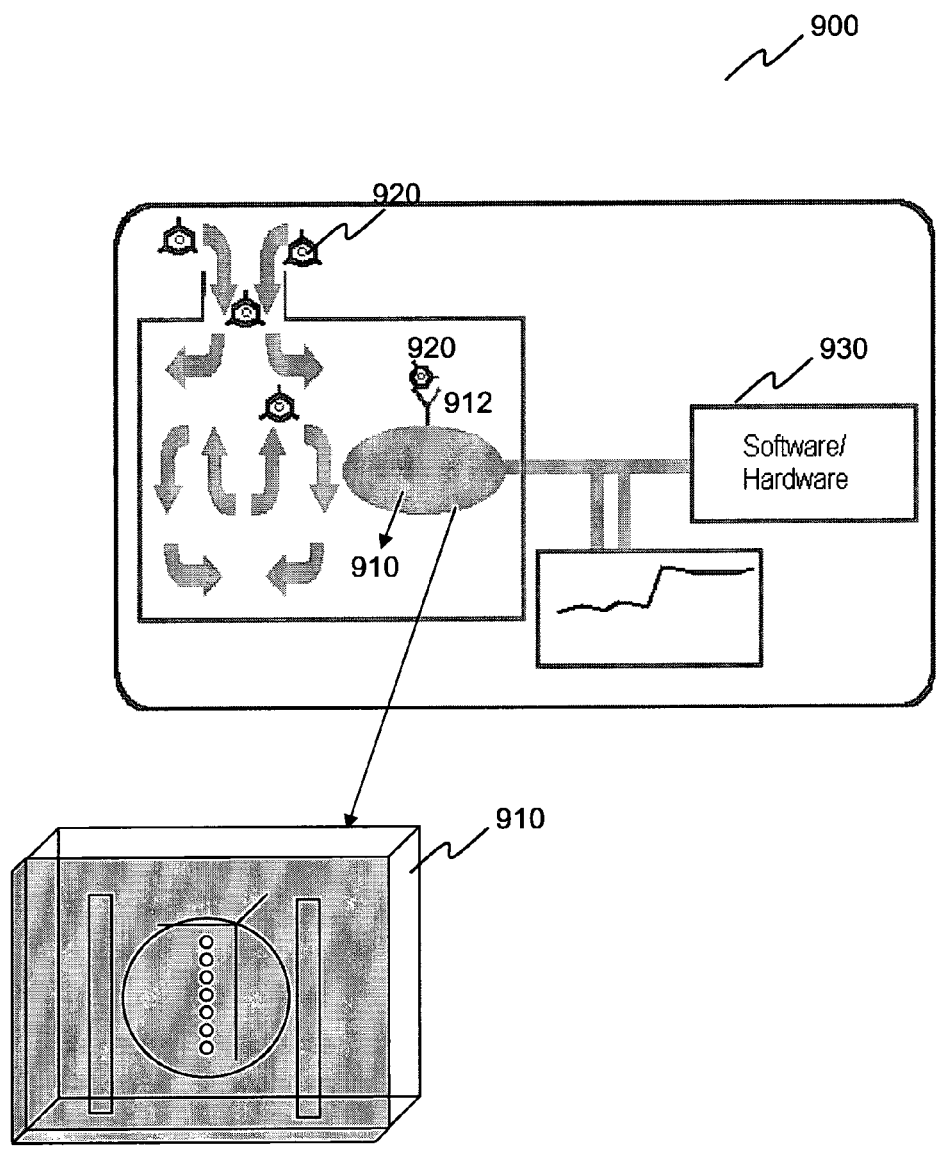
FIG. 9 shows an optical sensing system according to an embodiment of the invention.

FIG. 9 shows an optical sensing system 900 which may be used to detect explosives or drugs according to an embodiment of the invention.

As shown in FIG. 9, the optical resonator 910 as described in the above embodiment is included in the optical sensing system 900. When the air or fluid containing the analyte 920, in this example, the explosive or drug molecules 920, is flowing through the optical resonator 910, the analyte interacts with the capture element 912 provided within the hole of the optical resonator 910 and/or at the outer surface of the optical resonator 910. Such an interaction causes a change of the optical property of the optical resonator 910, which can be detected by a detector 930. The detector 930 may include software or hardware or both for detecting the existence of explosive or drug molecules.

The optical resonator as described in the above embodiments may be used in a plurality of applications, such as security detection of explosive and drugs, detection of land mines, detection of bacteria and virus, medical diagnostics, environment monitoring, food safety, etc. The optical resonator may also be used as tunable modulator, tunable multiplexer, or strain sensor in other embodiments.

Figure 10:
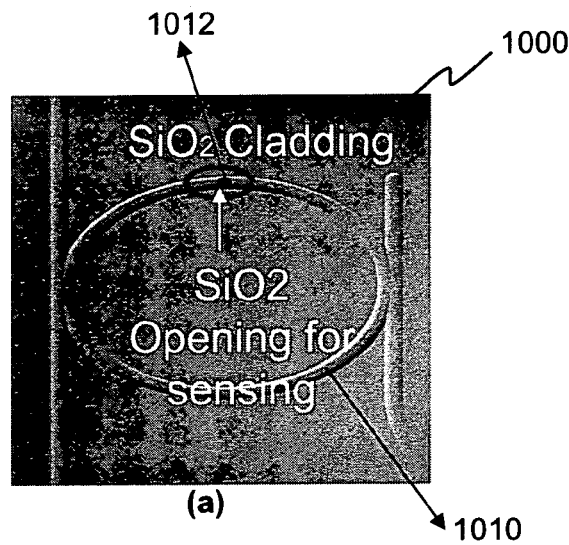
FIG. 10 shows the SEM pictures of a conventional optical resonator and an optical resonator in accordance with an embodiment of the invention.
Figure 10:
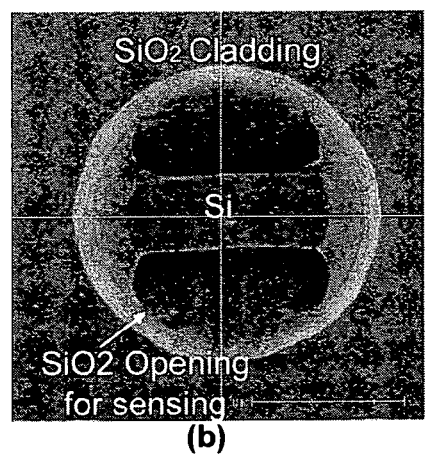
Figure 10:
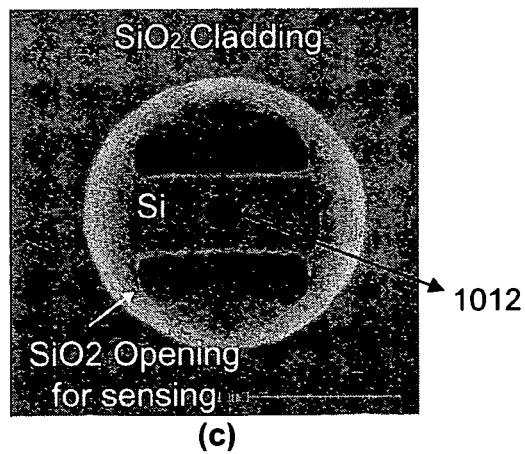

FIG. 10 shows the SEM pictures of a conventional optical resonator and an optical resonator in accordance with an embodiment of the invention.

FIG. 10(a) shows the SEM pictures of a fabricated optical resonator 1000 in accordance with an embodiment of the invention. The optical resonator 1000 was fabricated using SOI wafer with a top Si layer of 220 nm and buried oxide (BOX) of 2 um, followed by deposition of 3 um SiO2 top cladding layer. The sensing area 1012 was opened by hydrofluoric acid (HF) wet etching. FIG. 10(b) shows the top view of SiO2 opening sensing area for a conventional optical resonator, and FIG. 10(c) shows the top view of SiO2 opening sensing area for an optical resonator, e.g. the optical resonator 1000 of FIG. 10(a), including a hole 1012 formed within the closed loop 1010 of the optical resonator 1000.

The sample optical resonators of FIG. 10 are used in an experiment to verify the performance of the optical resonator. These samples were characterized with an automatic alignment system. Firstly, a bio-sensor sample was mounted on a fixed platform, and two lensed polarization maintaining fibers were placed in respective high-precision three-dimensionally adjustable stages. Diameter of the focus spots of the lensed fibers is about 2.5 um. For efficient fiber-waveguide coupling, the facets of the samples had been polished by deep etch in the fabrication process. Light was coupled into the sample from a tunable laser through a lensed fiber, and the light was collected at the other end of the sample by the other fiber. An IR camera was used to assist the alignment and observe the output mode profiles of the samples. After the alignment of fiber-waveguide-fiber, the spectral of the sample optical resonators were scanned and recorded. The wavelength range of the scanning light is from 1510 nm to 1612 nm and the scanning step is 20 pm (minimum scanning step is 5 pm).

Figure 11:
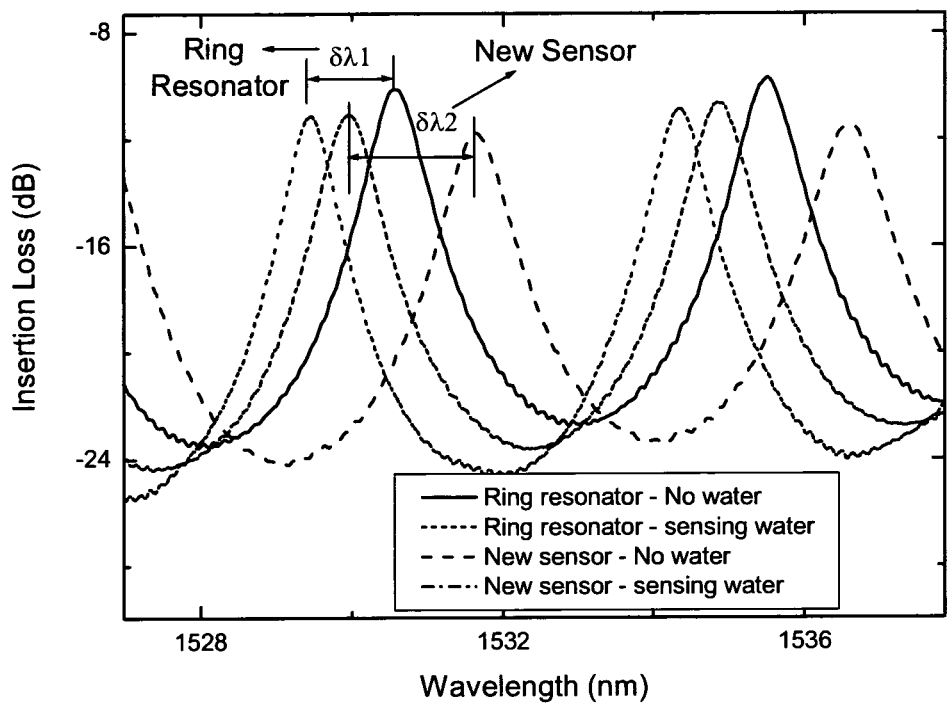
FIG. 11 shows experimental results of a conventional optical resonator and an optical resonator in accordance with an embodiment of the invention.

Pure water used as the analyte was put into sensing area, and the resonance frequency change before and after the usage of pure water was measured. FIG. 11 shows characterization results and the comparison of sensing performance between a conventional optical resonator of FIG. 10(b) and the optical resonator of FIG. 10(c) in accordance with an embodiment of the invention.

As shown in FIG. 11, $\delta\lambda 1$ represents the resonance frequency change of the conventional optical resonator before and after the pure water putting into sensing area, and $\delta\lambda 2$ represents the resonance frequency change of the optical resonator of the embodiment of the invention before and after the pure water putting into sensing area. The optical resonator in accordance with the embodiment of the invention has much bigger change in resonance frequency as compared to conventional optical resonator, which means that the optical resonator in accordance with the embodiment of the invention has higher sensitivity to small amount of analytes.

The performance of the optical resonator according to the embodiment of the invention is also simulated. The optical resonator 100 of FIG. 1A is used, wherein the waveguide width of the microring 102 is 500 nm and the radius of the microring 102 is 5 um. The radius of the cylinder hole 104 is 100 nm and the refractive index of the cylinder hole 104 is 1. Three structures were simulated with finite-difference time-domain method, wherein the first one is a conventional microring resonator without any hole or analyte, the second one is a microring resonator having an air hole with a radius of 100 nm on the microring waveguide, and the third one is a microring resonator with a 50 nm protein with a refractive index of 1.45 inserted in the air hole.

Figure 12:
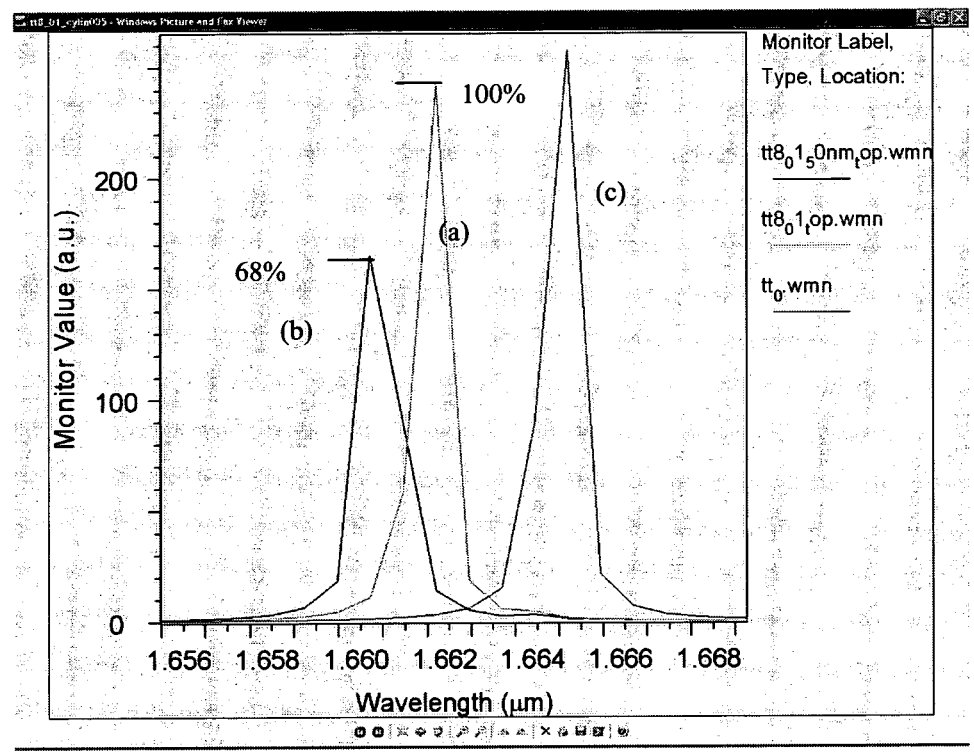
FIG. 12 shows simulation results of a conventional optical resonator and an optical resonator in accordance with an embodiment of the invention.

The simulation results are shown in FIG. 12, wherein (a) represents resonance wavelength peaks for the optical resonator having an air hole, (b) represents resonance wavelength peaks for the optical resonator having a hole containing a 50 nm protein with a refractive index of 1.45, and (c) represents resonance wavelength peaks for the conventional optical resonator. As shown in FIG. 12, there is a significant change in the resonance frequency of optical resonator having a hole after putting a sample particle with a diameter of 50 nm and a refractive index of 1.45 (simulating small amount of protein) into the hole. While no resonant frequency change is shown when the same sample particle is put on the conventional microring resonator, since the effective index change induced by the tiny 50 nm sample particle on the top of a conventional microring resonator is negligible. The simulation results show that the optical resonator according to the embodiment of the present invention has high sensitivity to small amount of analytes as compared to conventional microring and microdisk resonators.

The hole in the optical resonator is used to provide a path for light-matter interaction and does not need to be accurately fabricated.

Figure 13:
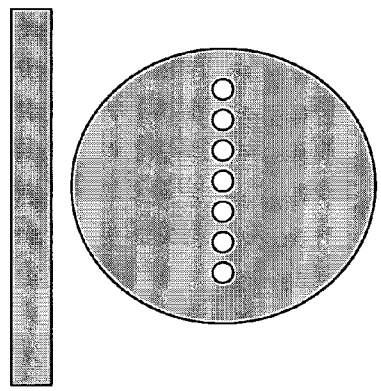
FIG. 13 shows the simulation results for an optical resonator in accordance with another embodiment of the invention.
Figure 13:
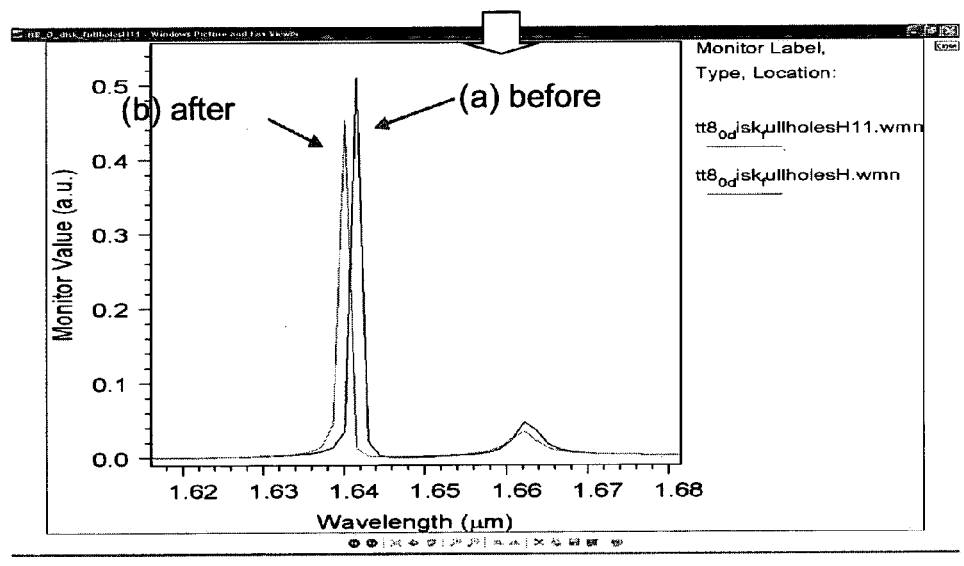

FIG. 13 shows the simulation results for optical resonators in accordance with another embodiment of the invention.

FIG. 13(a) shows the microdisk resonator in accordance with an embodiment of the invention, which is similar to the microdisk resonators of FIG. 3(b).

FIG. 13(b) shows the results of the resonance frequency changes of the optical resonator when the refractive index of the optical resonator in FIG. 13(a) changes by 0.1. As seen, the change of the resonance frequency of the optical resonator is about 20 nm. The optical resonator in FIG. 13(a) may be used to detect large amount of analytes, for example.

The optical resonator and the optical sensing system in accordance with the embodiments of the invention provide an ultra-high sensitivity to small amount of analytes, thereby reducing the amount of analytes needed to be used. In addition, the optical resonator and the optical sensing system in accordance with the embodiments of the invention have a structure which can be easily fabricated at low cost.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. An optical resonator, comprising
an input optical waveguide, and
a closed loop coupled to the input optical waveguide and adapted to receive light from the input optical waveguide,
wherein within a portion of the closed loop at least one hole is formed,
wherein the at least one hole is adapted such that an analyte can be introduced into the hole.

2. The optical resonator of claim 1, wherein the closed loop is embodied by a microring, a microdisk, or a microsphere.

3. The optical resonator of claim 1, wherein the closed loop is adapted to receive light with a wavelength on resonance with the optical resonator.

4. The optical resonator of claim 1, wherein each of the input optical waveguide and the closed loop comprises a guiding layer, and the guiding layer is sandwiched in between a top cladding layer and a bottom cladding layer.

5. The optical resonator of claim 4, wherein the guiding layer comprises a material selected from a group consisting of silicon, silicon nitride, silicon dioxide and polymer.

6. The optical resonator of claim 4, wherein the refractive index of the guiding layer is higher than the refractive index of the cladding layers.

7. The optical resonator of claim 1, wherein the at least one hole is adapted to be filled with a material having optical properties being different from optical properties of an analyte to be detected.

8. The optical resonator of claim 1, wherein the at least one hole is adapted to be filled with a material having optical properties being changeable in response to an interaction with an analyte to be detected.

9. The optical resonator of claim 1, wherein the at least one hole is adapted to be filled with a material being adapted to decompose or evaporate in response to an interaction with an analyte to be detected.

10. The optical resonator of claim 1, wherein the optical resonator is adapted to get into contact with an analyte at the outer surface of the optical resonator.

11. The optical resonator of claim 1, wherein at least one capture element is provided at the inner surface of the hole and/or at the outer surface of the optical resonator to interact with an analyte provided in the hole and/or in a surrounding area of the optical resonator, respectively.

12. The optical resonator of claim 11, wherein the at least one capture element is selected from a group consisting of antibody, enzyme, nucleic acid, cell receptor, micro-organism.

13. The optical resonator of claim 1, wherein the dimension of the at least one hole is in the order of nanometers to microns.

14. The optical resonator of claim 1, wherein the closed loop is embodied by a microring, the diameter of the at least one hole being smaller than two third of waveguide width of the microring.

15. The optical resonator of claim 14, wherein the diameter of the at least one hole is half of the waveguide width of the microring.

16. An optical sensing system, comprising:
a source of light,
at least one optical resonator comprising
an input optical waveguide adapted to guide light received from the source of light, and
a closed loop which is coupled to the input optical waveguide and which is adapted to receive light from the input optical waveguide, wherein within a portion of the closed loop at least one hole is formed, and wherein the at least one hole is adapted such that an analyte can be introduced into the hole, and
at least one detector coupled to the optical resonator to measure a parameter of the optical resonator responsive to an interaction of an analyte with the optical resonator.

17. The optical sensing system of claim 16, wherein the optical resonator further comprises an output optical waveguide, wherein the output optical waveguide is coupled to the closed loop and is adapted to receive output light from the closed loop, and wherein the output optical waveguide is coupled to the detector and is adapted to guide the output light to the detector.

18. The optical sensing system of claim 16, further comprising
a signal processor adapted to compare the measured parameter with a reference parameter;
a reference optical resonator comprising
a reference input optical waveguide adapted to guide light received from the source of light, and
a reference closed loop which is coupled to the reference input optical waveguide and which is adapted to receive light from the reference input optical waveguide, wherein within a portion of the reference closed loop at least one hole is formed, and
a reference detector coupled to the reference optical resonator to measure a reference parameter of the reference optical resonator.

19. A tunable modulator, a tunable multiplexer, or a strain sensor comprising the optical resonator of claim 1.

* * * * *

UNITED STATES PATENT AND TRADEMARK OFFICE
CERTIFICATE OF CORRECTION

PATENT NO.         : 8,538,214 B2                                      Page 1 of 1
APPLICATION NO.    : 12/993325
DATED              : September 17, 2013
INVENTOR(S)        : X. Chen et al.

It is certified that error appears in the above-identified patent and that said Letters Patent is hereby corrected as shown below:

On the title page of the patent, line 22:
  "PCT Filed:   Jun. 29, 2008"
Should be
  --PCT Filed:  May 29, 2008--

Signed and Sealed this
Twenty-sixth Day of November, 2013

Margaret A. Focarino
*Commissioner for Patents of the United States Patent and Trademark Office*